(12) United States Patent
Lynch et al.

(10) Patent No.: US 8,911,408 B2
(45) Date of Patent: Dec. 16, 2014

(54) PIVOTING JOINT INFUSION SYSTEM WITH SEAL

(75) Inventors: George R. Lynch, Coppell, TX (US); Allen E. Brandenburg, Dripping Springs, TX (US); Andrew Nelson, Dallas, TX (US); Gilles Petitjean, Issoudun (FR)

(73) Assignee: Applied Diabetes Research, Inc., Carrollton, TX (US)

( * ) Notice: Subject to any disclaimer, the term of this patent is extended or adjusted under 35 U.S.C. 154(b) by 796 days.

(21) Appl. No.: 12/952,780

(22) Filed: Nov. 23, 2010

(65) Prior Publication Data

US 2011/0112481 A1    May 12, 2011

Related U.S. Application Data

(63) Continuation of application No. 11/473,254, filed on Jun. 22, 2006, now Pat. No. 7,862,545, which is a continuation of application No. 10/463,629, filed on Jun. 17, 2003, now Pat. No. 7,083,597, which is a continuation-in-part of application No. 09/896,149, filed on Jun. 29, 2001, now Pat. No. 6,579,267.

(60) Provisional application No. 60/259,971, filed on Jan. 5, 2001.

(51) Int. Cl.
| | | |
|---|---|---|
| *A61M 5/178* | (2006.01) | |
| *A61M 5/142* | (2006.01) | |
| *A61M 39/02* | (2006.01) | |
| *B01D 39/16* | (2006.01) | |
| *A61M 5/158* | (2006.01) | |

(52) U.S. Cl.
CPC ... *A61M 5/14244* (2013.01); *A61M 2005/1581* (2013.01); *B01D 2239/0225* (2013.01); *B01D 2239/0659* (2013.01); *B01D 2239/045* (2013.01); *A61M 5/158* (2013.01); *A61M 2005/14252* (2013.01); *B01D 2239/0636* (2013.01); *B01D 2239/0208* (2013.01); *B01D 2239/0414* (2013.01); *B01D 2239/0663* (2013.01); *A61M 39/02* (2013.01); *B01D 2239/0233* (2013.01); *B01D 2239/0216* (2013.01); *B01D 39/163* (2013.01); *A61M 2005/1587* (2013.01); *A61M 5/14248* (2013.01); *B01D 2239/0471* (2013.01)
USPC ............ 604/167.05; 604/164.01; 604/164.04; 604/167.01; 604/167.03

(58) Field of Classification Search
CPC .......... A61M 2005/14252; A61M 2005/1581; A61M 2005/1587; A61M 39/02; A61M 5/14244; A61M 5/14248; A61M 5/158; A61M 39/0247; A61M 2039/0258; A61M 2039/0273; A61M 25/02; A61M 25/0606; A61M 25/0102; A61M 25/0097
USPC ................... 604/32, 93.01, 161, 164.01, 158, 604/164.02, 164.04, 164.07, 604/167.01–167.03, 167.05, 167.06, 533, 604/537–539
See application file for complete search history.

(56) References Cited

U.S. PATENT DOCUMENTS

| | | |
|---|---|---|
| 3,547,119 A | 12/1970 | Hall et al. |
| 3,739,778 A | 6/1973 | Monestere, Jr. et al. |

(Continued)

*Primary Examiner* — Aarti B Berdichevsky
*Assistant Examiner* — Laura Schell
(74) *Attorney, Agent, or Firm* — Jackson Walker, LLP

(57) ABSTRACT

An infusion system for delivery of therapeutic fluids from a remote source into a patient's body. The system has an infusion assembly, a rotating pivot joint member, a fluid connector assembly, and a sealing assembly retained within the infusion assembly between the housing of the infusion assembly and the rotating pivot joint member. The seal reduces leakage of fluids. The rotating joint may be pivoted to three distinct positions to allow for emplacement on the patient, delivery of the therapeutic fluid to the patient, and protected, sealed closure of the fluid channels to avoid patient fluid backflow.

16 Claims, 3 Drawing Sheets

(56) References Cited

U.S. PATENT DOCUMENTS

| | | | |
|---|---|---|---|
| 3,996,923 | A | 12/1976 | Guerra |
| 4,106,491 | A | 8/1978 | Guerra |
| 4,126,133 | A | 11/1978 | Schwartz |
| 4,258,940 | A | 3/1981 | Fudge |
| 4,311,136 | A | 1/1982 | Weikl et al. |
| 4,311,137 | A | 1/1982 | Gerard |
| 4,418,944 | A | 12/1983 | Haines et al. |
| 4,430,081 | A | 2/1984 | Timmermans |
| 4,531,937 | A | 7/1985 | Yates |
| 4,645,495 | A | 2/1987 | Vaillancourt |
| 4,755,173 | A | 7/1988 | Konopka et al. |
| 4,936,833 | A | 6/1990 | Sams |
| 5,019,054 | A | 5/1991 | Clement et al. |
| 5,098,394 | A | 3/1992 | Luther |
| 5,176,662 | A | 1/1993 | Bartholomew et al. |
| 5,201,717 | A | 4/1993 | Wyatt et al. |
| 5,242,411 | A | 9/1993 | Yamamoto |
| 5,257,980 | A | 11/1993 | Van Antwerp et al. |
| 5,281,206 | A | 1/1994 | Lopez |
| 5,300,045 | A | 4/1994 | Plassche, Jr. |
| 5,330,450 | A | 7/1994 | Lopez |
| 5,376,071 | A | 12/1994 | Henderson |
| 5,427,145 | A | 6/1995 | Grabenkort |
| 5,545,143 | A | 8/1996 | Fischell |
| 5,545,152 | A | 8/1996 | Funderburk et al. |
| 5,613,663 | A | 3/1997 | Schmidt et al. |
| 5,814,020 | A | 9/1998 | Gross |
| 5,848,990 | A | 12/1998 | Cirelli et al. |
| 5,851,197 | A | 12/1998 | Marano et al. |
| D404,482 | S | 1/1999 | Falk et al. |
| 5,858,001 | A | 1/1999 | Tsais et al. |
| 5,968,011 | A * | 10/1999 | Larsen et al. ............ 604/288.02 |
| 5,980,506 | A | 11/1999 | Mathiasen |
| 6,017,328 | A | 1/2000 | Fischell et al. |
| 6,056,718 | A | 5/2000 | Funderburk et al. |
| 6,093,172 | A | 7/2000 | Funderburk et al. |
| 6,095,997 | A | 8/2000 | French et al. |
| 6,186,982 | B1 | 2/2001 | Gross et al. |
| 6,213,973 | B1 | 4/2001 | Eliasen et al. |
| 6,248,093 | B1 | 6/2001 | Moberg |
| 6,302,866 | B1 | 10/2001 | Marggi |
| 6,355,021 | B1 | 3/2002 | Nielsen et al. |
| 6,419,699 | B1 * | 7/2002 | Schuessler ................. 623/11.11 |
| 6,482,186 | B1 | 11/2002 | Douglas et al. |
| D471,272 | S | 3/2003 | Douglas et al. |
| D472,316 | S | 3/2003 | Douglas et al. |
| D472,630 | S | 4/2003 | Douglas et al. |
| 6,585,695 | B1 | 7/2003 | Adair et al. |
| 6,629,949 | B1 | 10/2003 | Douglas |
| 6,641,566 | B2 | 11/2003 | Douglas et al. |
| 6,659,982 | B2 | 12/2003 | Douglas et al. |
| 6,673,440 | B2 | 1/2004 | Douglas et al. |
| 6,685,674 | B2 | 2/2004 | Douglas et al. |
| D488,230 | S | 4/2004 | Ignotz et al. |
| 6,752,787 | B1 | 6/2004 | Causey, III et al. |
| 6,800,071 | B1 | 10/2004 | McConnell et al. |
| 6,817,990 | B2 | 11/2004 | Yap et al. |
| 6,854,620 | B2 | 2/2005 | Ramey |
| 6,923,791 | B2 | 8/2005 | Douglas |
| 7,056,302 | B2 | 6/2006 | Douglas |
| 7,063,684 | B2 | 6/2006 | Moberg |
| 7,083,597 | B2 | 8/2006 | Lynch et al. |
| 7,211,068 | B2 | 5/2007 | Douglas |
| 2002/0045867 | A1 | 4/2002 | Nielsen et al. |
| 2002/0123724 | A1 | 9/2002 | Douglas et al. |
| 2002/0173748 | A1 | 11/2002 | McConnell et al. |
| 2002/0173769 | A1 * | 11/2002 | Gray et al. .................... 604/506 |
| 2003/0125672 | A1 | 7/2003 | Adair et al. |
| 2003/0163090 | A1 | 8/2003 | Blomquist et al. |
| 2004/0003493 | A1 | 1/2004 | Adair et al. |
| 2004/0085215 | A1 | 5/2004 | Moberg et al. |
| 2004/0092873 | A1 | 5/2004 | Mobert |
| 2005/0021000 | A1 | 1/2005 | Adair et al. |

* cited by examiner

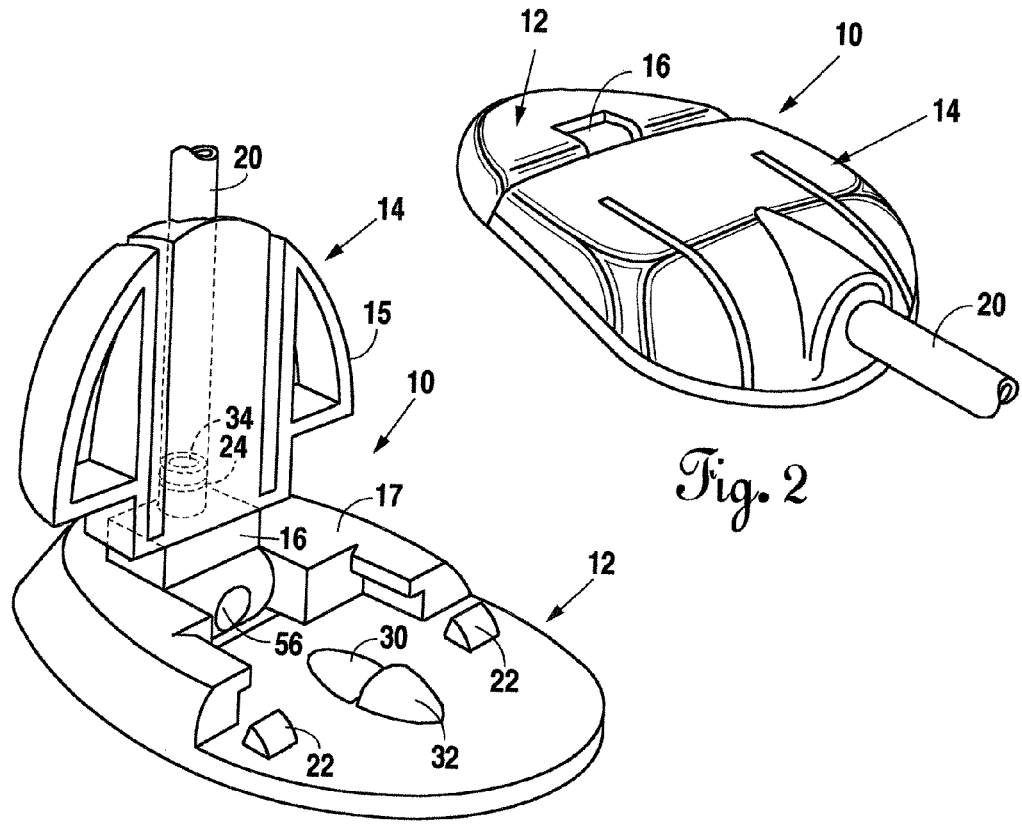
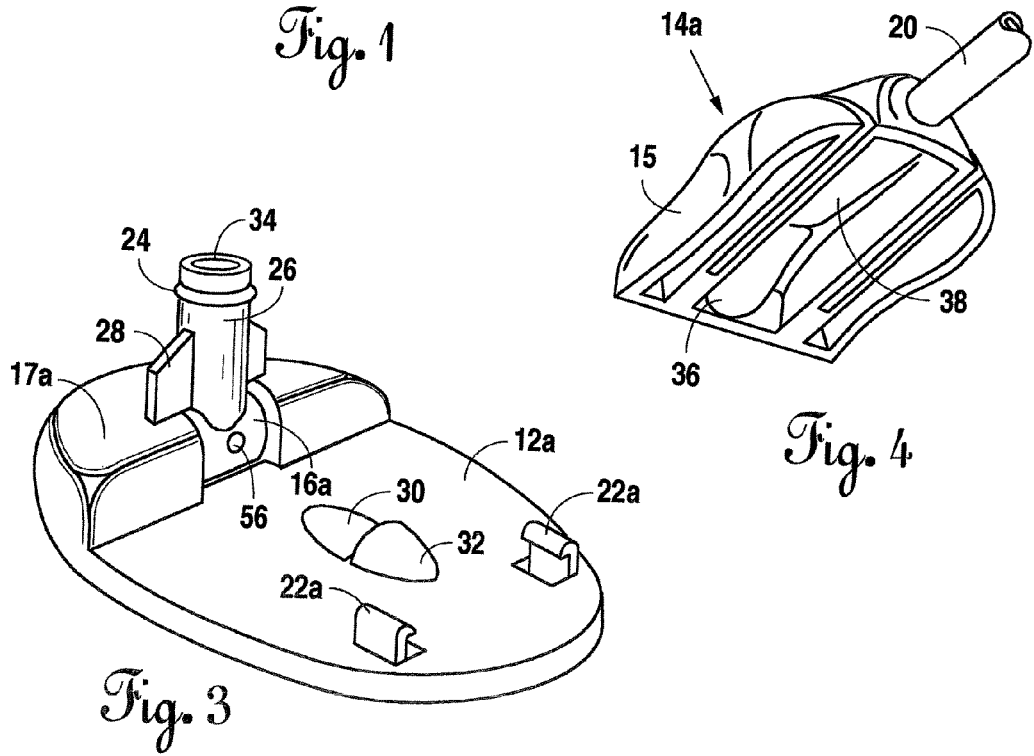

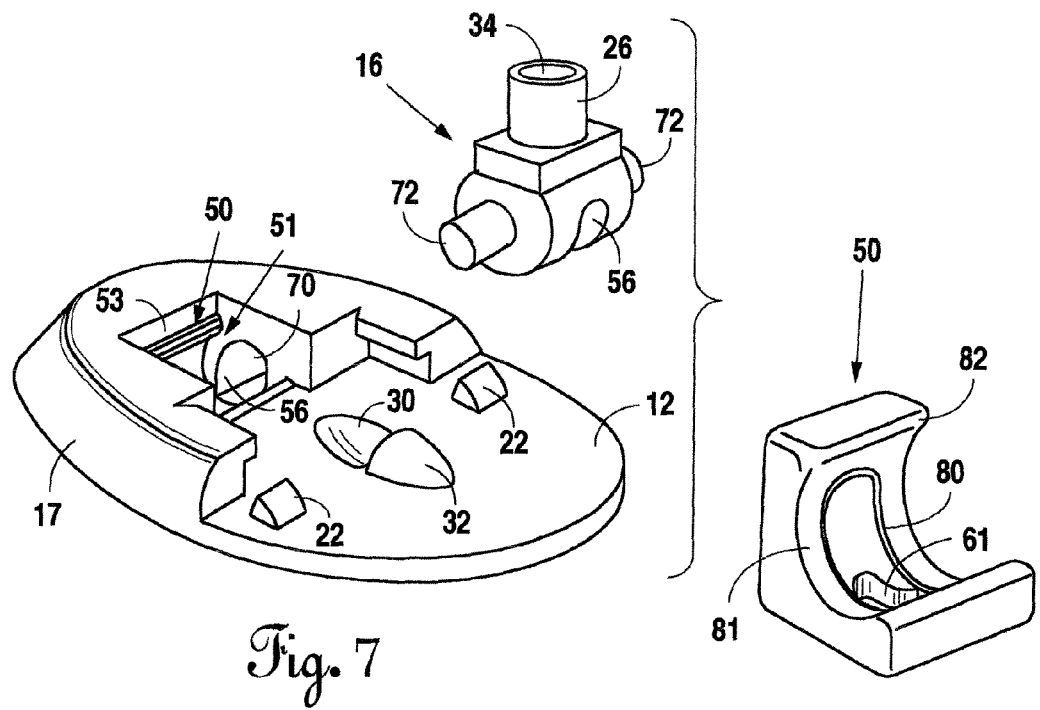
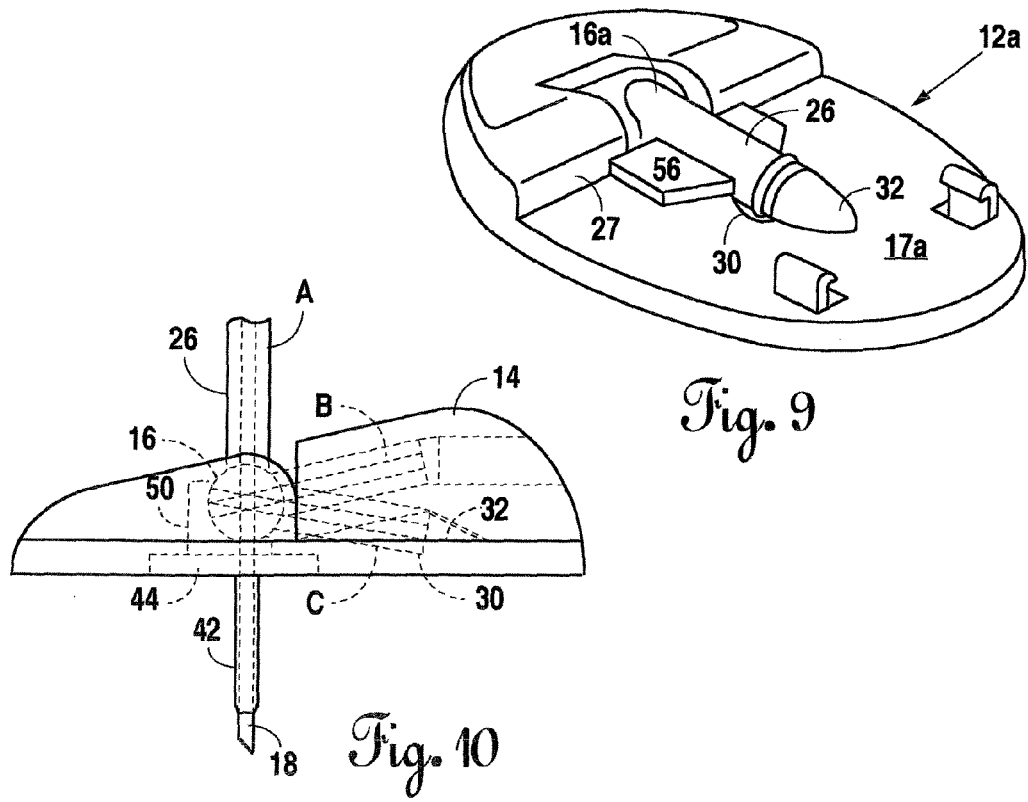

PIVOTING JOINT INFUSION SYSTEM WITH SEAL

This Ser. No. 12/952,780 application is a continuation application of continuation-in-part application Ser. No. 11/473,254, filed Jun. 22, 2006; which is a continuation of Ser. No. 10/463,629, filed Jun. 17, 2003, now U.S. Pat. No. 7,083,597, issued on Aug. 1, 2006, which is a continuation-in-part of U.S. patent application Ser. No. 09/896,149, filed Jun. 29, 2001, now U.S. Pat. No. 6,579,267, issued Jun. 17, 2003, which claims priority to U.S. Provisional Application No. 60/259,971, filed Jan. 5, 2001, all of which are incorporated herein by reference for all purposes.

FIELD OF THE INVENTION

The present invention relates to an improved system for subcutaneous delivery of fluid to a patient. More particularly, the present invention relates to an infusion system having an improved sealing subsystem cooperating with a rotating pivot joint member that delivers the fluid from a remote source to a delivery cannula of the main infusion assembly of the system.

BACKGROUND OF THE INVENTION

Prior art infusion sets or systems provide numerous ways for engaging a fluid connector to a base to deliver a therapeutic fluid subcutaneously to a patient. Most of these prior art systems are plagued with leaking connections and inefficient ways to allow the patient to disconnect the fluid connector from the base without a backflow of fluid from the patient through the base and back into the environment.

The present invention provides an improved sealing subsystem incorporated into a pivoting or rotating "ball" joint that moves from an emplacement position to an infusion or delivery position to a disconnected, protected, closed position.

BRIEF DESCRIPTION OF THE DRAWINGS

FIG. 1 illustrates a perspective view of the present invention system with the fluid connector attached to the rotating pivot member in a vertical, non-delivery position.

FIG. 2 shows the fluid connection moved to an operating, infusion or delivery position and locked in engagement with the base unit.

FIG. 3 shows the base unit of the present invention with the rotating pivot member in the vertical position to accept an emplacement needle assembly.

FIG. 4 is a bottom perspective view of the fluid connector of the present invention with a fluid delivery tube attached thereto.

FIG. 7 is an exploded perspective view of the base unit of the present invention showing the seal assembly and the rotating pivot member.

FIG. 8 is a detailed perspective view of the seal assembly of the present invention.

FIG. 9 illustrates a perspective view of the base assembly and the rotating pivot member of the present invention rotated to a protected closed position to prevent backflow of patient fluids.

FIG. 10 shows three distinct positions of the rotating or pivoting member of the present invention, namely, the emplacement position, the infusion position, and the protected, closed position.

DETAILED DESCRIPTION OF THE PREFERRED EMBODIMENT OF THE PRESENT INVENTION

Figure 5:
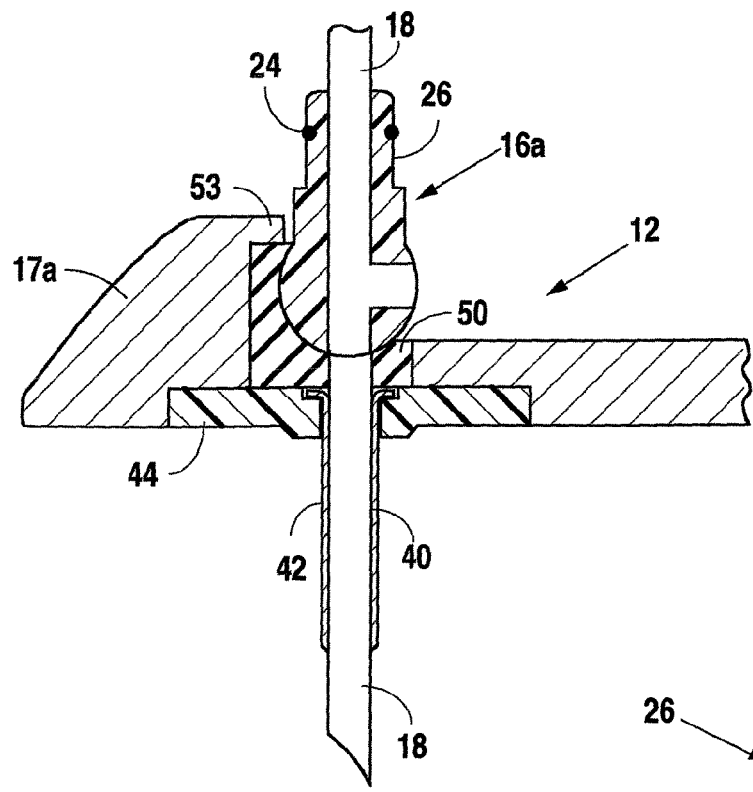
FIG. 5 illustrates a partial cross sectional side elevation plan view of the present invention in a first emplacement position.

FIG. 1 is a perspective view of the infusion system 10 of the present invention. In FIG. 1, the main infusion unit 12 is shown with the fluid connector assembly 14 attached to the rotating pivot joint member 16. The joint member 16 is rotatably attached to the housing 17 of unit 12. The emplacement needle 18 (FIG. 5) has been withdrawn and the connector assembly is still in an upright or vertical position. Therapeutic fluid from a remote source (not shown but well known in the art) such as a wall or rack hung bottle or plastic fluid bag may be delivered through delivery tube 20 to the connector assembly 14 and into the patient. However, the preferred procedure is for the needle to be withdrawn and the joint member 16 slightly rotated downwardly to misalign the emplacement channel 54 (FIG. 5A) and the injection channel 40. This will prevent or significantly avoid a backflow of patient fluids as will be discussed below. The connector assembly 14 is then attached to the joint member 16 and the rotating joint member and the connector assembly 14 are to be rotated about joint member 16 to the horizontal delivery or infusion position shown in FIG. 2. In FIG. 2, the fluid connector 14 has rotated about joint 16 and has locked onto the locking tabs 22 (FIG. 1) of the main infusion unit 12 and is thereby held securely in place.

FIG. 3 shows a slightly modified main infusion unit 12*a* having a pivot joint member 16*a* with an O-ring seal 24 on neck section 26 of the joint. Neck 26 has opposing wings 28 which serve to ensure an aligned rotation of the joint 16*a* about the housing 17*a*. The wings further function to ensure proper alignment of the connector assembly 14*a* to the main infusion unit 12*a*. FIG. 9 additionally shows how wings 28 hold the neck 26 in a third distinct position. FIG. 3 also illustrates a recess section 30 and cover 32 in housing 17*a*. As will be described below, the recess 30 accepts the top section of neck 26 in a third rotated position of joint 16*a* and cover 32 shields, protects, and seals the central fluid channel 34 in the joint member 16*a* when the fluid connector has been removed from the rotating pivot joint member 16*a*.

FIG. 4 illustrates in a perspective view the underside or bottom side of the fluid connector 14*a* which attaches at a near end 36 to the rotating pivot joint member. It should be noted in FIG. 4 that the fluid delivery channel 38 in connector 14*a* has a slight approach angle variation as will be described in more detail in the discussion of FIG. 10.

The structural arrangement or relationship of the joint member 16*a* to housing 17*a* is seen in the partial cross sectional view of FIG. 5. FIG. 5 shows the joint 16*a* in a first emplacement position with an emplacement needle 18 extending through the rotating joint 16*a*, through the injection channel 40 of cannula 42, and subcutaneously piercing the skin of the patient. A retainer plate 44 holds the cannula 18 within the housing 17*a*. The emplacement of the needle and how the main infusion unit may be affixed to the patient are well understood as described in U.S. Pat. No. 6,579,267. Also shown in FIG. 5 is the placement and retention of sealing assembly 50 within housing 17. FIG. 8 shows the sealing assembly in greater detail.

Figure 5A:
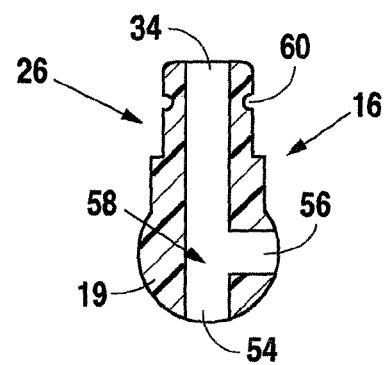

The rotating pivot joint member 16*a* is shown in a side elevational cross sectional view in FIG. 5A. Central fluid channel 34, needle emplacement channel 54, and fluid infusion channel 56 intersect in a central portion 58 of the joint 16a. Grooves 60 are provided for O-ring seals in the neck section.

Figure 6:
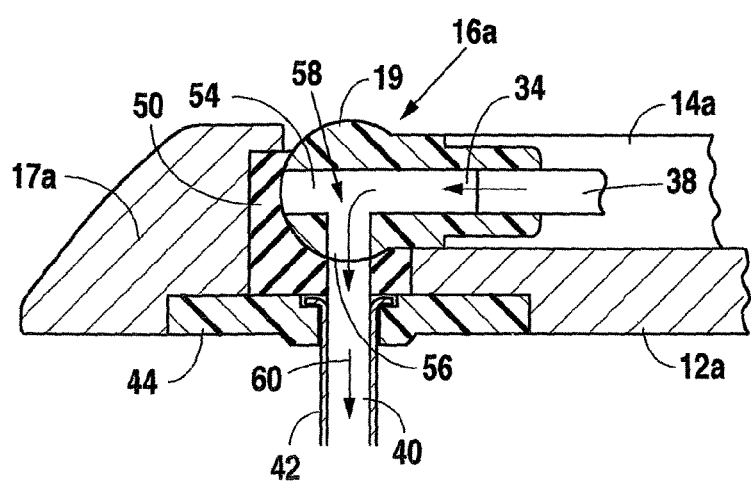
FIG. 6 shows the pivot member and base unit of FIG. 5 with the emplacement needle withdrawn and the rotating pivot member rotated to a second infusion or delivery position.

FIG. 6 shows the pivot member or joint 16a with the emplacement needle withdrawn and fluid connector assembly 14a attached. The joint 16a is rotated to an infusion or delivery position with the infusion channel 56 aligned with the injection channel 40 in cannula 42. Thus, therapeutic fluid 60 from the remote source flows through fluid delivery channel 38 in connector assembly 14a into central fluid channel 34, into infusion channel 56 through cannula injection channel 40 into the patient. As would be understood by one of skill in the art, the connector assembly 14a is secured to the main infusion unit 12a by the locking tabs 22 urging against the body 15 of the connector assembly.

In FIG. 7 an exploded perspective illustration is provided of pivot joint member 16, housing 17, sealing assembly 50, and rotating pivot joint member receiving chamber 51. The joint 16 has axial rotation journals or ears 72 which engage in slots 70 in the receiving chamber 51. The sealing assembly also fits snugly between the housing 17 and the joint 16 when the system is fully assembled. Turning to FIGS. 5 and 6 it may be seen that elastomeric seal 50 is urged beneath overhanging ledge 53 of housing 17 and is thereby further held in position. When the joint 16 is rotatably secured in the chamber 51, the seal 50 provides a sealing surface for the joint body 19 to sealingly rotate upon. In FIG. 8, the L-shaped seal assembly 50 has an orifice 61 to allow the needle or fluid to pass through. A raised rib 80 along the inner surface 81 of the seal may be used to provide an additionally tight seal. It should be understood that the use of various cooperating materials may be used in the construction of the seal 50 and the joint body 19. A hard-to-soft surface interface may be employed. The seal may be softer than the joint or vice versa. Two hard surfaces with cooperating coefficients of friction may be employed.

A protected, closed, and sealed third position of the rotating pivot joint member 16a is shown in FIG. 9. When the patient removes the connector assembly 14 or 14a from the pivot joint 16 or 16a, the alignment of the injection channel and the infusion channel in the joint would allow patient fluids to flow back through the infusion assembly and leak or flow into the environment. However, a unique feature of the present invention allows the user to rotate the pivot joint 16a downwardly to a third distinct position placing the neck 26 and central fluid channel 34 into recess 30 with cover 32 sealing off the open channel 34. Thus, no patient fluids backflow through the system. FIG. 9 also illustrates that alignment wings 28 also function to stop the downward rotation of the joint 16a; and, because they rub or slide tightly along housing shoulder 27 of the main infusion assembly 12a, the neck 26 is retained in the recess during the user's movement.

The distinct positions of the rotating "ball" pivot joint member 16 are illustrated in FIG. 10. In position A, the emplacement needle may be guided through the appropriate channels in the joint to allow the main infusion unit 12 to be attached to the patient. In position B, the needle has been removed and the fluid connector assembly 14 attached to the joint 16. The fluid channels in the connector assembly and the joint are aligned to allow for the therapeutic fluid to flow from the remote source through the delivery tube, through the joint and cannula channels to the patient. In position C, the fluid connector assembly 14 has been removed and the joint rotated further downwardly to rest in recess 30 with cover 32 sealing the fluid channel 34. Additionally, the further rotation of the joint misaligns the infusion channel 56 of the joint from the injection channel 40 of the cannula thereby further sealing off the backflow of any patient fluids through the system to the environment.

It may be seen in FIG. 10 that the sealing assembly 50 directly engages over 90° of the surface of the pivot joint 16 in any one of the distinct positions; but, because of the rotatability of the joint, over 270° of the ball joint surface is sealingly urged against the seal assembly 50. This feature provides for a more efficient sealing of the channels in the joint thereby reducing leakage problems associated with the prior art.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

The invention claimed is:

1. An infusion system for delivery of a therapeutic fluid from a remote source into a patient's body comprising:
 a main infusion unit having a housing, a cannula with an injection channel, said cannula attached vertically at an underside of said main infusion unit, [a first fluid channel in communication with said cannula,] and a rotating joint member receiving surface;
 a rotating joint member having a fluid channel, a separate needle emplacement channel, and a separate fluid infusion channel generally perpendicular to the fluid channel and the needle emplacement channel, said rotating joint member adapted to be received upon and rotatable with said joint member receiving surface; and
 a fluid connector assembly having a fluid delivery channel, said fluid connector assembly removably attachable to an end of said rotating joint member such that said fluid delivery channel aligns with and is in fluid communication with said fluid channel of said rotating joint member, said fluid connector assembly attachable at a remote end to a delivery tube attached to said remote source of said therapeutic fluid;
 whereby an emplacement needle may be extended when said rotating joint member is vertical, through said fluid channel and said needle emplacement channel of said rotating joint member and through said injection channel of said cannula to subcutaneously pierce said patient;
 wherein said rotating joint member is rotatable about 90° in an axis perpendicular to said cannula from a first vertical emplacement position to a second horizontal delivery position after said emplacement needle has been withdrawn from said patient and said fluid connector assembly has been attached to said rotating joint member, said second delivery position aligning said fluid infusion channel such that it is in fluid communication with said injection channel of said cannula to deliver said therapeutic fluid to said patient;
 wherein said rotating joint member is rotatable to a third position, the third position for preventing flow of therapeutic fluid to the patient's body or the flow of fluids from the patient's body out of the rotating joint member.

2. The infusion system of claim 1, wherein the main infusion unit further includes a cover adapted to protect an opening to said fluid channel in said rotating joint member when said rotating joint member is rotated to the third position.

3. The infusion system of claim 1, wherein a central portion of said rotating joint member is a ball joint.

4. The infusion system of claim 3, wherein said rotating joint member includes ears attached to the ball joint.

5. The infusion system of claim 1, wherein said rotating joint member receiving surface comprises a fluid sealing member cooperating with said fluid connector assembly and said rotating joint member to provide a fluid tight seal when the fluid connector assembly is engaged with the rotating joint member.

6. The infusion system of claim 1, further including means to releasably lock said fluid connector assembly to said rotating joint member when said fluid connector assembly is in said second delivery position.

7. The infusion system of claim 1, wherein the main infusion unit has walls defining a cutout and the fluid connector assembly has walls dimensioned for receipt into the cutout when the fluid connector assembly is in the second delivery position.

8. The infusion system of claim 1, wherein the main infusion unit, rotating joint member, and fluid connector assembly are all septumless.

9. The infusion system of claim 1, wherein a central portion of said rotating joint member is a ball joint; wherein said rotating joint member receiving surface comprises a fluid sealing member cooperating with said fluid connector assembly and said rotating joint member to provide a fluid tight seal when the fluid connector assembly is engaged with the rotating joint member; and further including means to releasably lock said fluid connector assembly to said rotating joint member when said fluid connector assembly is in said second delivery position.

10. The infusion system of claim 9, wherein the main infusion unit further comprises a recess in said housing to receive and retain the rotating joint member when the rotating joint member is in the third position.

11. The infusion system of claim 9, wherein the main infusion unit has walls defining a cutout and the fluid connector assembly has walls dimensioned for receipt into the cutout when the fluid connector assembly is in the second delivery position.

12. The infusion system of claim 9, wherein the main infusion unit, rotating joint member, and fluid connector assembly are all septumless.

13. The infusion system of claim 1, further including means to releasably lock said fluid connector assembly to said rotating joint member when said fluid connector assembly is in said second delivery position; and, wherein a central portion of said rotating joint member is a ball joint.

14. The infusion system of claim 13, wherein the central portion of said rotating joint member is a ball joint.

15. The infusion system of claim 13, wherein said rotating joint member includes ears attached to the ball joint.

16. The infusion system of claim 13, wherein the central portion of said rotating joint member is a ball joint; and further including means to releasably lock said fluid connector assembly to said rotating joint member when said fluid connector assembly is in said second delivery position.

* * * * *